(12) United States Patent
Fridriksson et al.

(10) Patent No.: US 11,557,400 B2
(45) Date of Patent: *Jan. 17, 2023

(54) MACHINE LEARNING TO IDENTIFY LOCATIONS OF BRAIN INJURY

(71) Applicant: UNIVERSITY OF SOUTH CAROLINA, Columbia, SC (US)

(72) Inventors: Julius Fridriksson, Blythewood, SC (US); Christopher Rorden, Blythewood, SC (US)

(73) Assignee: University of South Carolina, Columbia, SC (US)

( * ) Notice: Subject to any disclaimer, the term of this patent is extended or adjusted under 35 U.S.C. 154(b) by 207 days.

This patent is subject to a terminal disclaimer.

(21) Appl. No.: 17/141,436

(22) Filed: Jan. 5, 2021

(65) Prior Publication Data

US 2021/0125727 A1    Apr. 29, 2021

Related U.S. Application Data

(62) Division of application No. 16/217,152, filed on Dec. 12, 2018, now Pat. No. 10,916,348.

(Continued)

(51) Int. Cl.
| | |
|---|---|
| *G16H 50/30* | (2018.01) |
| *G16H 20/40* | (2018.01) |
| *G16H 50/70* | (2018.01) |
| *G16H 50/50* | (2018.01) |
| *G06N 20/00* | (2019.01) |
| *A61N 1/36* | (2006.01) |
| *A61B 5/00* | (2006.01) |
| *A61B 5/369* | (2021.01) |

(52) U.S. Cl.
CPC ............ *G16H 50/30* (2018.01); *G06N 20/00* (2019.01); *G16H 20/40* (2018.01); *G16H 50/50* (2018.01); *G16H 50/70* (2018.01); *A61B 5/369* (2021.01); *A61B 5/7264* (2013.01); *A61N 1/36025* (2013.01)

(58) Field of Classification Search
CPC ............................................... G06Q 50/20–26
See application file for complete search history.

(56) References Cited

U.S. PATENT DOCUMENTS

| | | | |
|---|---|---|---|
| 9,349,103 B2 | 5/2016 | Eberhardt et al. | |
| 10,028,694 B2 | 7/2018 | Jones et al. | |

(Continued)

FOREIGN PATENT DOCUMENTS

WO   WO 2017/106498    6/2017

OTHER PUBLICATIONS

American Stroke Association. (2017) http://www.stroke.org.

*Primary Examiner* — Neal Sereboff
(74) *Attorney, Agent, or Firm* — Dority & Manning, P.A.

(57) ABSTRACT

The present disclosure provides systems and methods that include or otherwise leverage a machine-learned brain injury location model to predict locations of brain injury in a patient based on test data associated with the patient, such as, for example, behavioral test data. For example, the machine-learned brain injury location model can be trained on training data associated with a corpus of patients, where the training data includes sets of example test data (e.g., behavioral test data) respectively labeled with ground truth brain injury locations.

13 Claims, 5 Drawing Sheets

Related U.S. Application Data

(60) Provisional application No. 62/597,475, filed on Dec. 12, 2017.

(56) References Cited

U.S. PATENT DOCUMENTS

| | | |
|---|---|---|
| 2012/0184840 A1 | 7/2012 | Najarian et al. |
| 2016/0331327 A1 | 11/2016 | Kozloski et al. |
| 2018/0115598 A1 | 4/2018 | Shariat et al. |
| 2018/0330714 A1 | 11/2018 | Paulik et al. |
| 2019/0180878 A1* | 6/2019 | Fridriksson ............ G16H 50/70 |
| 2021/0375480 A1* | 12/2021 | Mahon ................... G16H 20/30 |
| 2022/0148738 A1* | 5/2022 | Sughrue ................. A61B 5/742 |

* cited by examiner

MACHINE LEARNING TO IDENTIFY LOCATIONS OF BRAIN INJURY

RELATED APPLICATIONS

This application is a divisional application of U.S. patent application Ser. No. 16/217,152, filed Dec. 12, 2018, which claims priority to and the benefit of U.S. Provisional Patent App. No. 62/597,475, filed Dec. 12, 2017, and titled "Machine Learning to Identify Locations of Brain Injury," each of which is incorporated by reference herein in its entirety.

FIELD

The present disclosure relates generally to detection and treatment of brain injury. More particularly, the present disclosure relates to machine-learned models that predict locations of brain injury in a patient based on test data associated with the patient, such as, for example, behavioral test data.

BACKGROUND

Brain stimulation is an emerging clinical tool that can enhance the effect of rehabilitation of persons with brain damage. One example type of brain stimulation is electrical brain stimulation. One example electrical brain stimulation technique is transcranial electrical brain stimulation such as, for example, transcranial direct current stimulation (tDCS) and, as another example, transcranial alternating current stimulation. For example, tDCS treatment has been shown to have positive effects for individuals suffering from post-stroke aphasia. Other example types of brain stimulation include magnetic brain stimulation and infrared brain stimulation. Similar to electrical brain stimulation, magnetic brain stimulation and infrared brain stimulation can also be performed in a transcranial fashion.

One major challenge to applying transcranial brain stimulation is that it should not be applied directly over brain areas that are damaged. Therefore, the clinician needs to know where in the brain a patient has damage, so that the clinician can avoid applying transcranial brain stimulation to such locations.

Typically, identifying locations of brain injury in a patient requires a magnetic resonance imaging (MRI) or computed tomography (CT) scan. However, MRI and CT scans are relatively expensive, as they rely upon the use of specialized and complex imaging devices. Furthermore, most brain damage rehabilitation clinics do not have quick access to MM or CT scanning devices and instead must refer the patient to an alternative provider to obtain the MM or CT scan, which represents additional cost, inconvenience, and expenditure of time.

As such, due to cost and practicality, the use of MRI or CT is a major obstacle to the use of transcranial brain stimulation as a common tool used in rehabilitation settings.

SUMMARY

Aspects and advantages of embodiments of the present disclosure will be set forth in part in the following description, or can be learned from the description, or can be learned through practice of the embodiments.

One example aspect of the present disclosure is directed to a computing system. The computing system includes a machine-learned brain injury location model trained to identify one or more locations of brain injury in a patient based on test data associated with the patient. The computing system includes one or more processors and one or more non-transitory computer-readable media that store instructions that, when executed by the one or more processors, cause the one or more processors to perform operations. The operations include obtaining the test data associated with the patient. The operations include inputting the test data into the machine-learned brain injury location model. The operations include receiving, as an output of the machine-learned brain injury location model, one or more predicted locations of brain injury associated with the patient.

Another example aspect of the present disclosure is directed to a method. The method includes obtaining, by a computing system comprising one or more computing devices, test data associated with a patient. The method includes inputting, by the computing system, the test data into a machine-learned brain injury location model. The method includes receiving, by the computing system as an output of the machine-learned brain injury location model, one or more predicted locations of brain injury associated with the patient. The method includes performing a transcranial brain stimulation procedure on the patient, wherein a positioning of the transcranial brain stimulation procedure is determined based at least in part on the one or more predicted locations of brain injury output by the machine-learned brain injury location model.

Another example aspect of the present disclosure is directed to one or more tangible, non-transitory computer-readable media that collectively store instructions that, when executed, cause a computing device perform operations. The operations include obtaining training data associated with a corpus of patients, wherein the training data comprises sets of example test data respectively labeled with ground truth brain injury locations. The operations include inputting the sets of example test data into a machine-learned brain injury location model. The operations include receiving a predicted brain injury location for each set of example test data as an output of the machine-learned brain injury location model. The operations include evaluating an objective function that evaluates a difference between the predicted brain injury location for each set of example test data and the ground truth brain injury location for such set of example test data. The operations include adjusting one or more parameters of the machine-learned brain injury location model to improve the objective function.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

DETAILED DESCRIPTION

Example aspects of the present disclosure are directed to systems and methods that include or otherwise leverage a machine-learned brain injury location model to predict locations of brain injury in a patient based on test data associated with the patient, such as, for example, behavioral test data. For example, the machine-learned brain injury location model can be trained on training data associated with a corpus of patients, where the training data includes sets of example test data (e.g., behavioral test data) respectively labeled with ground truth brain injury locations.

More particularly, as described in the background section above, typically, identifying locations of brain injury in a patient requires a magnetic resonance imaging (MRI) or computed tomography (CT) scan. However, MRI and CT scans are relatively expensive and are often unavailable in typical brain injury rehabilitation settings.

To overcome these problems, the present disclosure provides systems, methods, and associated algorithms that allow clinicians to estimate the location and extent of brain damage in a patient without the use of CT or MM. Therefore, the clinician can safely perform a transcranial brain stimulation procedure (e.g., transcranial electrical brain stimulation such as tDCS) without the use of CT or MM, thereby reducing the cost associated with the procedure and also increasing the availability of the procedure. More specifically, the clinician is able to avoid stimulating directly over damaged brain tissue without using MRI or CT.

With reference now to the figures, example embodiments of the present disclosure will be discussed in further detail.

Figure 1:
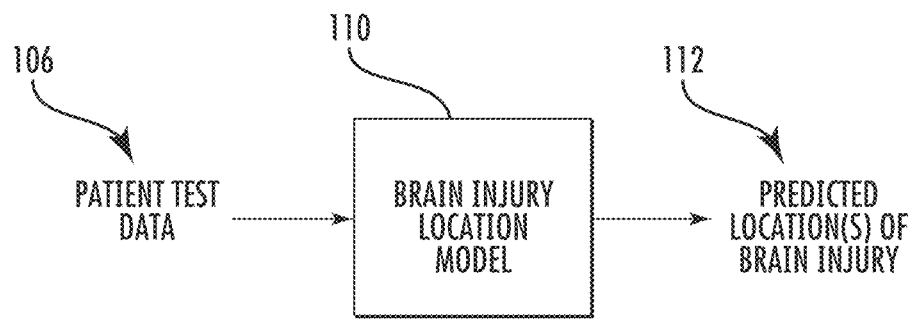
FIG. 1 depicts an example processing workflow for identification of locations of brain injury according to example embodiments of the present disclosure.

FIG. 1 depicts an example processing workflow for identification of locations of brain injury according to example embodiments of the present disclosure. In particular, the processing workflow includes or otherwise leverages a machine-learned brain injury location model 110. In some instances, the processing workflow illustrated in FIG. 1 can be referred to as "symptom-lesion-mapping" (SLM).

A clinician or other individual can administer or caused to be administered one or more tests to a patient to generate test data 106 associated with the patient. The clinician can input the test data 106 into a computing system or the test data 106 can be collected by the computing system (e.g., through the use of one or more sensor devices).

As one example, the one or more tests can include one or more behavioral tests that produce behavioral test data 106. The behavioral test data 106 can describe the patient's performance relative to the one or more behavioral tests. The behavioral tests can include any form of test that evaluates the patient's language skills or abilities, perceptual skills or abilities, motor skills or abilities, emotional skills or abilities, or other behavioral characteristics.

As one example, the behavioral tests can include including showing imagery to a patient and asking the patient to describe the imagery. As another example, the behavioral tests can include showing the patient imagery of an object and asking the patient to identify (e.g., name) the object. As yet another example, the behavioral tests can include requesting that the patient perform a physical or motor task (e.g., brushing teeth, combing hair, writing name, etc.) and evaluating the patient's ability to perform the physical task.

As another example, the behavioral tests can include testing the patient's ability to detect and respond when different objects are presented on a display (e.g., electronic display screen). As yet another example, the behavioral tests can include testing the patient's ability to identify and select a target object included in a display that also includes a number of distraction objects.

The patient's responses to or performance relative to the behavioral tests can be manually evaluated (e.g., by the clinician providing a score) or can be automatically scored (e.g., number of correct selections on an automated or computerized test) or can be evaluated according to a predefined metric or scoring formula (e.g., completing a task in certain time periods results in a different scores being assigned).

As another example, the one or more tests can include one or more biometric tests that produce biometric data 106 collected from the patient's body. For example, the biometric data 106 can include electroencephalogram (EEG) data collected from the patient. As another example, the test data 106 associated with the patient can also include biomarker data, such as, for example, the age of the patient at a time of brain injury.

The computing system can input the test data 106 into the machine-learned brain injury location model 110. As examples, the machine-learned brain injury location model 110 can include a deep artificial neural network, a support vector machine, a decision tree, and/or a linear model.

The machine-learned brain injury location model 110 can output one or more predicted locations 112 of brain injury associated with the patient. Alternatively or additionally, the machine-learned brain injury location model 110 can output a predicted extent of brain injury associated with the patient. In some implementations, the predicted extent can be provided by providing locations in the form of a defined volume, area, or other spatial representation.

In particular, the locations 112 and/or extent of injury can be represented in a number of different fashions. As one example, the locations 112 can include identification of certain predefined brain regions (e.g., temporal lobe vs. frontal lobe) or any sub-regions thereof that have been damaged. As another example, the locations 112 can be identified by coordinates within the brain. For example, the locations 112 can be defined by volumes within the brain.

As another example, the machine-learned brain injury location model 110 and/or associated computing system components can output or otherwise generate and provide an injury visualization that visualizes the one or more predicted locations of brain injury (e.g., as shaded volumes within a visualization of a brain).

Figure 4A:
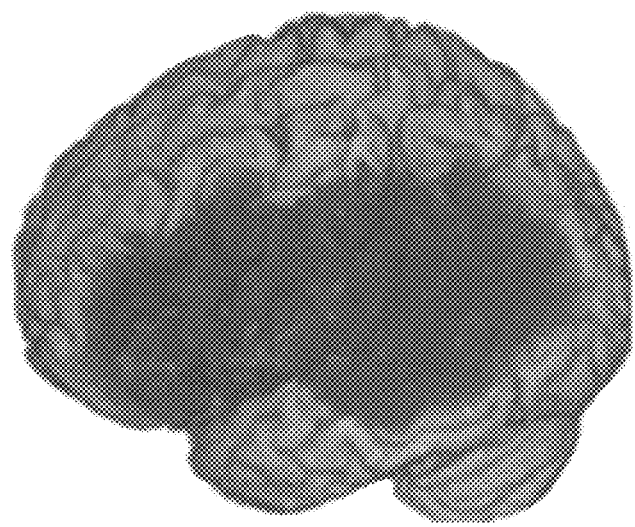
FIGS. 4A and 4B depict example injury visualizations according to example embodiments of the present disclosure.
Figure 4B:
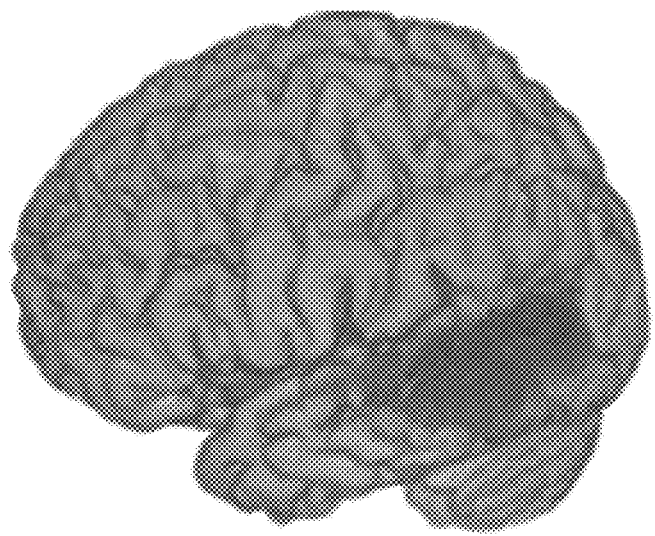

As examples, FIGS. 4A and 4B provide example injury visualizations that visualize one or more predicted locations of brain injury. In the example injury visualization of FIGS. 4A and 4B, regions with darker shading are predicted to have brain injury as such locations. Thus, the injury visualizations quickly present both the location and extent of brain injury in an easily understandable format.

Referring again to FIG. 1, in some implementations, the output of the machine-learned model 110 (e.g., injury visualizations) can further include or depict a probability information that describes, for each brain location 112, a probability that such location is associated with brain injury.

Figure 5:
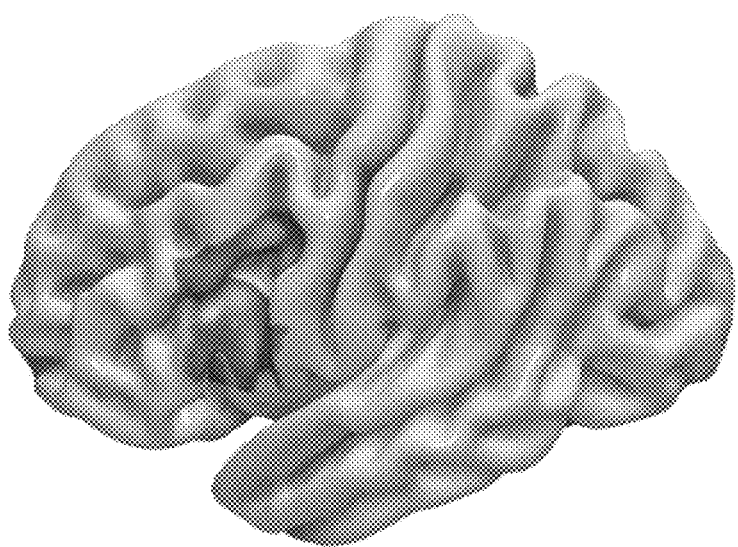
FIG. 5 depicts an example injury visualization that includes damage probability information according to example embodiments of the present disclosure.

As one example, FIG. 5 provides an example injury visualization that includes a color scheme that maps to a confidence/probability that a particular brain area has been compromised. Thus, the machine-learned model can provide, for each brain location, a confidence or probability that such location is associated with injury and, in some implementations, such probability information can be visualized; for example, using coloration according to a color scheme where certain colors map to certain probabilities.

Referring again to FIG. 1, in some implementations, the machine-learned brain injury location model 110 and/or associated computing system components can output or otherwise generate and provide a treatment guide that describes locations at which brain stimulation can be safely applied. The treatment guide can be provided in addition or alternatively to the injury visualizations described above.

Thus, the model 110 can predict locations 112 at which brain injury has occurred and, based on such predicted locations 112, a treatment guide can be generated that describes where to perform a brain stimulation procedure. For example, in some instances, the locations at which stimulation can be safely applied correspond to an inverse of the predicted locations 112 of brain injury. Thus, the systems and methods of the present disclosure can predict various anatomical features of the patient's brain, including, for example, lesion location, surviving eloquent regions, or other anatomical features.

In some implementations, the computing system can cause the treatment guide to be displayed on a display screen, so that the clinician is able to review the treatment guide while performing the stimulation procedure. As one example, in some implementations, the treatment guide can be or include a treatment visualization that visually illustrates the locations at which the stimulation procedure can or should be applied.

Figure 6:
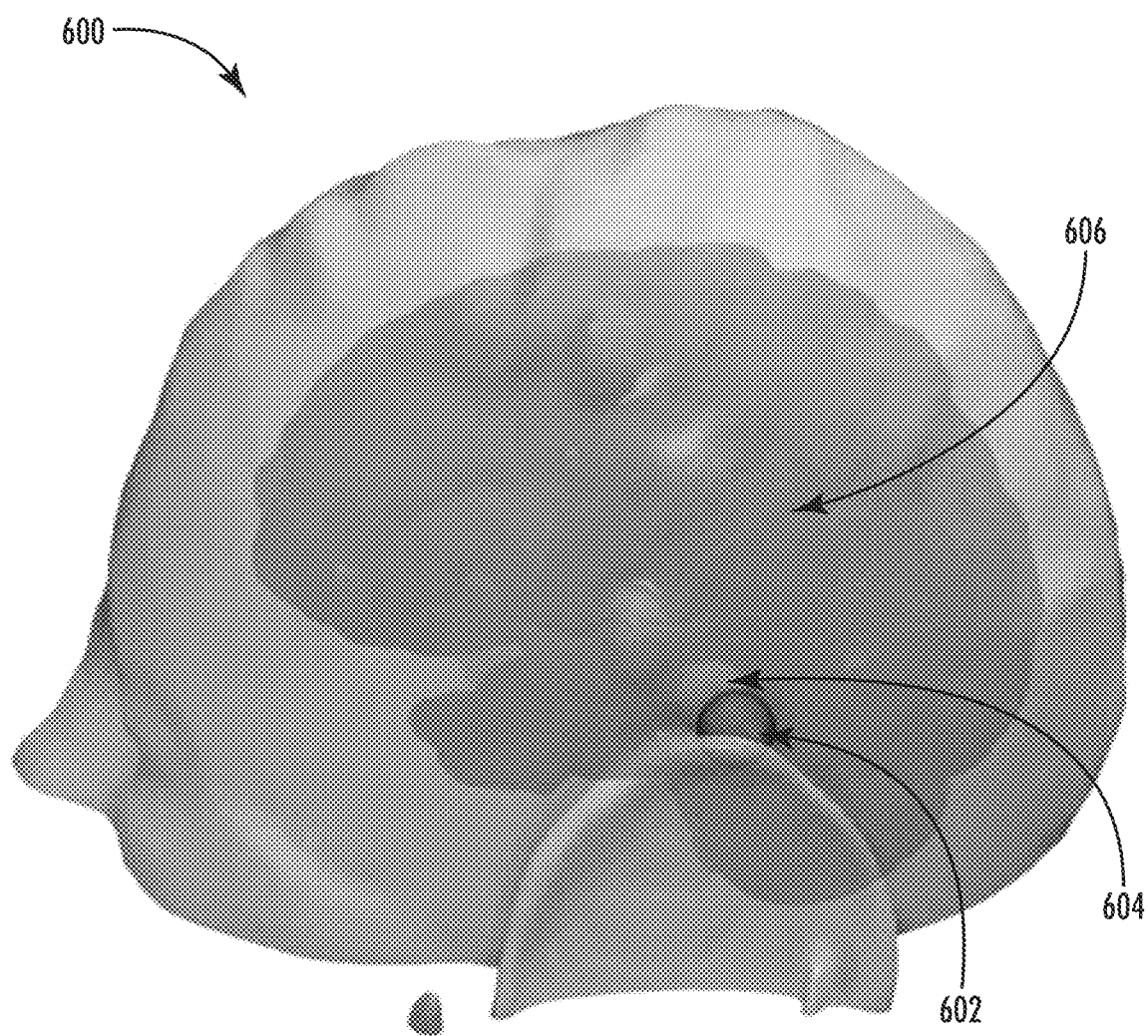
FIG. 6 depicts an example treatment visualization according to example embodiments of the present disclosure.

As one example, FIG. 6 provides an example treatment visualization 600 according to example embodiments of the present disclosure. In particular, the example treatment visualization 600 of FIG. 6 visualizes a scalp brain stimulation target location 602 above an estimated brain stimulation site 604 which is on the brain 606.

Referring again to FIG. 1, in some implementations, the injury visualizations and/or treatment visualizations can be interactive. For example, the visualizations can include three-dimensional renderings that a user (e.g., clinician) can interact with. As one example, the user can click, hold, and drag to rotate the brain about an axis. As another example, the user can zoom to review certain brain region in closer detail.

In some implementations, the computing system can provide the user (e.g., clinician) with the option of either using a generic head/brain model or to alternatively provide patient-specific data to enable personalized modeling, visualizations, etc. For example, the user can provide measurements of a patient's head size/shape. For example, the measurements can be manually obtained using various instruments (e.g., measuring tape) or the measurements can be obtained through an automated process such as photogrammetry. The measurements can be used to provide personalized visualization and the like. Further, in some implementations, the head measurements can be provided as input to the machine-learned model 110 to improve the accuracy of the injury location predictions.

Thus, in some implementations, the computing system can take clinical testing data as input and, in response, provide the clinician with a picture of the patient's head showing where the brain stimulation should be applied. One benefit of the described system is that it can guide the treatment and recovery expectations for people with brain injury without requiring expensive scans or the analysis of scans.

Figure 2:
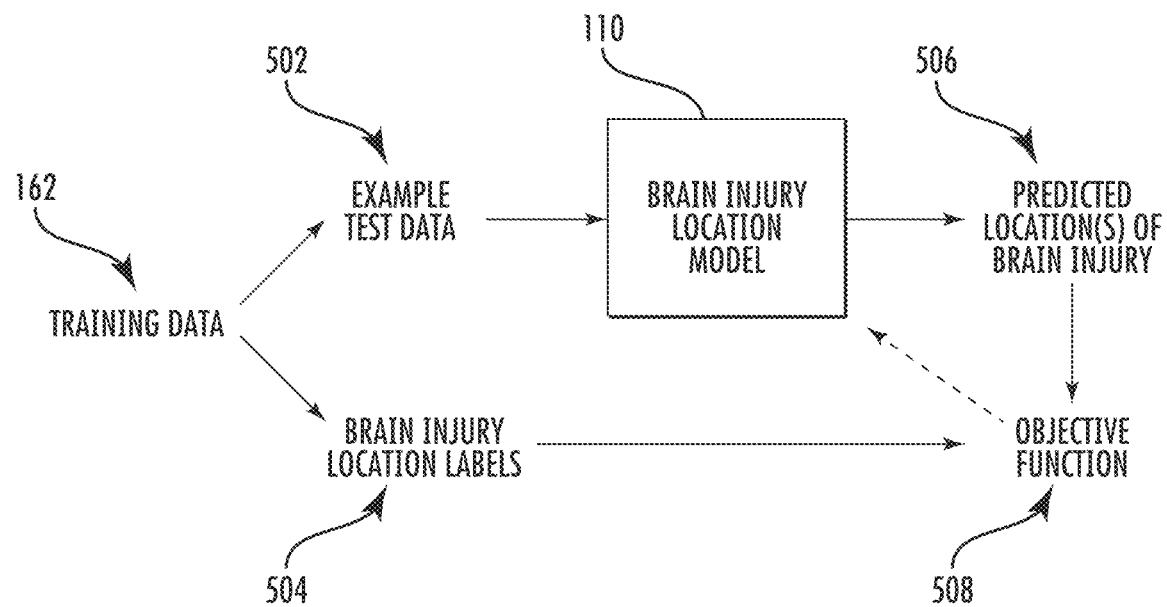
FIG. 2 depicts an example processing workflow for training a brain injury location model according to example embodiments of the present disclosure.

FIG. 2 depicts an example workflow for training a brain injury location model 110 according to example embodiments of the present disclosure. For example, the workflow can be performed by a machine learning computing system (e.g., the model trainer 160 of machine learning computing system 140, as described below with reference to FIG. 3).

Referring still to FIG. 2, in some implementations, the machine-learned brain injury location model 110 can be trained on training data 162. The training data 162 can includes sets of example test data 502 that are labelled with brain injury location labels 504. That is, the each set of example test data 502 can have an associated label 504 that describes locations of brain injury associated with a patient that generated the corresponding example test data 502.

The example test data 502 can include any of the types of test data described with reference to FIG. 1. The brain injury location labels 504 can describe the locations and/or extent of brain injury in any of the forms described with reference to FIG. 1. For example, the brain injury location labels 504 can mirror the format for which the predicted locations of brain injury are desired to be represented. As one example, if it is desired for the model 110 to predict location of brain injury in the form of injury visualizations, then the brain injury location labels 504 can be or can include ground truth injury visualizations associated with the example test data 502.

As one example, the training data 162 can be obtained from a database where clinical scores (e.g., on behavioral tests) are related to probability of having damage in brain areas typically injured by stroke.

Each set of example test data 502 can be input into the brain injury location model 110. In response, the model 110 can output one or more prediction locations of brain injury 506 for each set of example test data 502. An objective function 508 can evaluate a difference between the prediction location(s) 506 for each set of example test data 502 and the brain injury location label(s) 504 associated with such set of test data 502. For example, the prediction (e.g., injured or not injured) for each potential location (e.g., brain region) can be compared to the ground truth labels. As one example, the objective function can determine, for each pixel or voxel of a rendering of the brain, whether the prediction matches the label for such pixel or voxel, where non-matching pixels/voxels increase a loss value. The objective function 508 can be backpropagated through the brain injury location model 110 to train the model 110.

FIG. 2 illustrates one example supervised learning workflow. Other training techniques can be used in addition or alternatively to the example workflow shown in FIG. 2.

Figure 3:
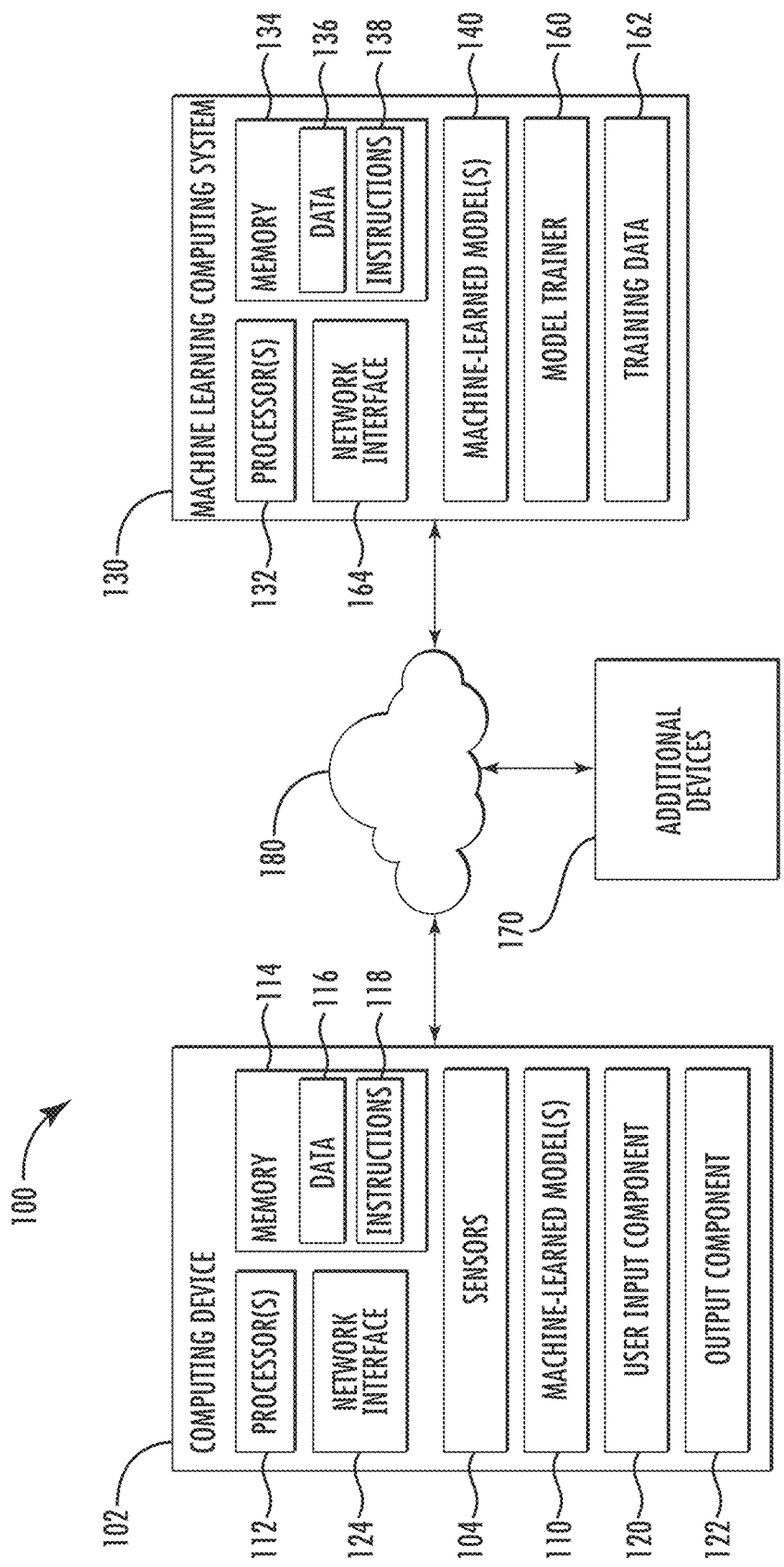
FIG. 3 depicts an example computing system for machine-learning-based brain injury location identification according to example embodiments of the present disclosure.

FIG. 3 depicts an example computing system 100 for machine-learning-based identification of brain injury locations according to example embodiments of the present disclosure. The example system 100 includes a computing device 102 and a machine learning computing system 130 that are communicatively coupled over a network 180.

The computing device 102 includes one or more processors 112 and a memory 114. The one or more processors 112 can be any suitable processing device (e.g., a processor core, a microprocessor, an ASIC, a FPGA, a controller, a microcontroller, etc.) and can be one processor or a plurality of processors that are operatively connected. The memory 114 can include one or more non-transitory computer-readable storage media, such as RAM, ROM, EEPROM, EPROM, one or more memory devices, flash memory devices, etc., and combinations thereof.

The memory 114 can store information that can be accessed by the one or more processors 112. For instance, the memory 114 (e.g., one or more non-transitory computer-readable storage mediums, memory devices) can store data 116 that can be obtained, received, accessed, written, manipulated, created, and/or stored. In some implementations, the computing device 102 can obtain data from one or more memory device(s) that are remote from the device 102.

The memory 114 can also store computer-readable instructions 118 that can be executed by the one or more processors 112. The instructions 118 can be software written in any suitable programming language or can be implemented in hardware. Additionally, or alternatively, the instructions 118 can be executed in logically and/or virtually separate threads on processor(s) 112.

For example, the memory 114 can store instructions 118 that, when executed by the one or more processors 112, cause the one or more processors 112 to perform any of the operations and/or functions described herein.

According to an aspect of the present disclosure, the computing device 102 can store or include one or more machine-learned models 110. For example, the models 110 can be or can otherwise include various machine-learned models such as a random forest classifier; a logistic regression classifier; a support vector machine; one or more decision trees; a neural network; and/or other types of models including both linear models and non-linear models. Example neural networks include feed-forward neural networks, recurrent neural networks (e.g., long short-term memory recurrent neural networks), convolutional neural networks, or other forms of neural networks.

In some implementations, the computing device 102 can receive the one or more machine-learned models 110 from the machine learning computing system 130 over network 180 and can store the one or more machine-learned models 110 in the memory 114. The computing device 102 can then use or otherwise run the one or more machine-learned models 110 (e.g., by processor(s) 112).

The machine learning computing system 130 includes one or more processors 132 and a memory 134. The one or more processors 132 can be any suitable processing device (e.g., a processor core, a microprocessor, an ASIC, a FPGA, a controller, a microcontroller, etc.) and can be one processor or a plurality of processors that are operatively connected. The memory 134 can include one or more non-transitory computer-readable storage media, such as RAM, ROM, EEPROM, EPROM, one or more memory devices, flash memory devices, etc., and combinations thereof.

The memory 134 can store information that can be accessed by the one or more processors 132. For instance, the memory 134 (e.g., one or more non-transitory computer-readable storage mediums, memory devices) can store data 136 that can be obtained, received, accessed, written, manipulated, created, and/or stored. In some implementations, the machine learning computing system 130 can obtain data from one or more memory device(s) that are remote from the system 130.

The memory 134 can also store computer-readable instructions 138 that can be executed by the one or more processors 132. The instructions 138 can be software written in any suitable programming language or can be implemented in hardware. Additionally, or alternatively, the instructions 138 can be executed in logically and/or virtually separate threads on processor(s) 132.

For example, the memory 134 can store instructions 138 that when executed by the one or more processors 132 cause the one or more processors 132 to perform any of the operations and/or functions described herein.

In some implementations, the machine learning computing system 130 includes one or more server computing devices. If the machine learning computing system 130 includes multiple server computing devices, such server computing devices can operate according to various computing architectures, including, for example, sequential computing architectures, parallel computing architectures, or some combination thereof.

In addition or alternative to the model(s) 110 at the computing device 102, the machine learning computing system 130 can include one or more machine-learned models 140. For example, the models 140 can be or can otherwise include various machine-learned models such as a random forest classifier; a logistic regression classifier; a support vector machine; one or more decision trees; a neural network; and/or other types of models including both linear models and non-linear models. Example neural networks include feed-forward neural networks, recurrent neural networks (e.g., long short-term memory recurrent neural networks), convolutional neural networks, or other forms of neural networks.

As an example, the machine learning computing system 130 can communicate with the computing device 102 according to a client-server relationship. For example, the machine learning computing system 140 can implement the machine-learned models 140 to provide a web service to the computing device 102. For example, the web service can provide identification of brain injury locations as a service.

Thus, machine-learned models 110 can be located and used at the computing device 102 and/or machine-learned models 140 can be located and used at the machine learning computing system 130.

In some implementations, the machine learning computing system 130 and/or the computing device 102 can train the machine-learned models 110 and/or 140 through use of a model trainer 160. The model trainer 160 can train the machine-learned models 110 and/or 140 using one or more training or learning algorithms. One example training technique is backwards propagation of errors ("backpropagation").

In some implementations, the model trainer 160 can perform supervised training techniques using a set of labeled training data 162; for example, as described with reference to FIG. 2. In other implementations, the model trainer 160 can perform unsupervised training techniques using a set of unlabeled training data. The model trainer 160 can perform a number of generalization techniques to improve the generalization capability of the models being trained. Generalization techniques include weight decays, dropouts, or other techniques. The model trainer 160 can be implemented in hardware, software, firmware, or combinations thereof.

The computing device 102 can also include a network interface 124 used to communicate with one or more systems or devices, including systems or devices that are remotely located from the computing device 102. The network interface 124 can include any circuits, components, software, etc. for communicating with one or more networks (e.g., 180). In some implementations, the network interface 124 can include, for example, one or more of a communications controller, receiver, transceiver, transmitter, port, conductors, software and/or hardware for communicating data. Similarly, the machine learning computing system 130 can include a network interface 164.

The computing device 102 can also include one or more sensors 104. For example, the one or more sensors 104 can include any type of sensor useful to collect test data from a patient, including, for example, various forms of biometric data. As one example, the sensors 104 can include EEG sensors that collect EEG data.

The computing device 102 can also include a user input component 120. For example, the user input component 120 can include a microphone, a keypad, a keyboard, a click-wheel, buttons, and/or a touch-sensitive screen.

The computing device 102 can also include an output component 122. For example, the output component 122 can include a speaker, a haptic output component, and/or a display (e.g., a touch-sensitive display).

As another example, the computing device 102 can transmit information to one or more additional devices 170 (e.g., a brain stimulation application system, databases, etc.). The computing device 102 can communicate with the additional computing device(s) 170 over the network 180 and/or via a local, short-range wireless communication protocol (e.g., BLUETOOTH™).

The network(s) 180 can be any type of network or combination of networks that allows for communication between devices. In some embodiments, the network(s) can include one or more of a local area network, wide area network, the Internet, secure network, cellular network, mesh network, peer-to-peer communication link and/or some combination thereof and can include any number of wired or wireless links. Communication over the network(s) 180 can be accomplished, for instance, via a network interface using any type of protocol, protection scheme, encoding, format, packaging, etc.

FIG. 3 illustrates one example computing system 100 that can be used to implement the present disclosure. Other computing systems can be used as well. For example, in some implementations, the computing device 102 can include the model trainer 160 and the training dataset 162. In such implementations, the machine-learned models 110 can be both trained and used locally at the computing device 102. As another example, in some implementations, the computing device 102 is not connected to other computing systems.

The systems and methods of the present disclosure provide a number of technical effects and benefits. In particular, the systems and methods of the present disclosure enable the performance of brain stimulation procedures (e.g., transcranial electrical brain stimulation) without the need for a MM or CT scan to be performed. Thus, the systems and methods of the present disclosure significantly reduce the cost associated with brain stimulation procedures while also improving access to such procedures. As described above, brain stimulation procedures have been shown to have positive effects for individuals suffering from brain damage, such as, for example, post-stroke aphasia. Thus, the systems and methods of the present disclosure can significantly improve patient health outcomes overall.

As another example technical effect and benefit, the systems and methods of the present disclosure can identify locations of brain injury using extremely low computing resource expenditure. For example, as compared to complex imaging systems such as MRI and CT, the machine-learned-based systems described herein consume orders of magnitude less processing and memory resources. Thus, the present disclosure represents an improvement to the computing technology itself that is needed to identify brain injury locations.

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computing system, the computing system comprising:
    a machine-learned brain injury location model trained with training data to identify one or more locations of brain injury in a patient based on test data associated with the patient;
    one or more processors; and
    one or more non-transitory computer-readable media that store instructions that, when executed by the one or more processors, cause the one or more processors to perform operations, the operations comprising:
        obtaining training data associated with a corpus of patients, wherein the training data comprises sets of example test data respectively labeled with ground truth brain injury locations;
        inputting the sets of example test data into a machine-learned brain injury location model;
        obtaining the test data associated with the patient;
        inputting the test data into the machine-learned brain injury location model;
        receiving, as an output of the machine-learned brain injury location model, one or more predicted locations of brain injury associated with the patient;
        evaluating an objective function that evaluates a difference between the one or more predicted brain injury locations for each set of example test data and the ground truth brain injury location for such set of example test data;
        adjusting one or more parameters of the machine-learned brain injury location model to improve the objective function; and
        wherein a positioning of a transcranial brain stimulation procedure is determined based at least in part on the one or more predicted locations of brain injury output by the machine-learned brain injury location model.

2. The computing system of claim 1, wherein the test data associated with the patient comprises behavioral test data indicative of a performance of the patient on one or more behavioral tests.

3. The computing system of claim 1, wherein the test data associated with the patient comprises biometric data collected from a body of the patient.

4. The computing system of claim 1, wherein the test data associated with the patient comprises biomarker data associated with the patient.

5. The computing system of claim 4, wherein the biomarker data comprises an age of the patient at a time of brain injury.

6. The computing system of claim 1, wherein the operations further comprise:
receiving, as the output of the machine-learned brain injury location model, a predicted extent of brain injury associated with the patient.

7. The computing system of claim 1, wherein:
receiving, as the output of the machine-learned brain injury location model, the one or more predicted locations of brain injury associated with the patient comprises receiving, as the output of the machine-learned brain injury location model, an injury visualization that visualizes the one or more predicted locations of brain injury associated with the patient; and
the operations further comprise displaying the visualization on a display screen.

8. The computing system of claim 1, wherein the operations further comprise:
generating, based at least in part on the one or more predicted locations of brain injury output by the machine-learned brain injury location model, a treatment guide that describes locations for transcranial brain stimulation.

9. The computing system of claim 8, wherein the operations further comprise:
displaying the treatment guide on a display screen.

10. The computing system of claim 9, wherein the treatment guide comprises a treatment visualization that visually illustrates the locations for transcranial brain stimulation.

11. The computing system of claim 1, wherein the machine-learned brain injury location model comprises one or more of: a deep artificial neural network, a support vector machine, a decision tree, or a linear model.

12. The computing system of claim 1, wherein the one or more tangible, non-transitory computer-readable media cause the one or more processors to perform additional operations, the additional operations comprising:
evaluating an objective function that evaluates a difference between the predicted brain injury location for each set of example test data and the ground truth brain injury location for such set of example test data; and
adjusting one or more parameters of the machine-learned brain injury location model to improve the objective function.

13. The computing system of claim 1, wherein the computing system is configured to perform a transcranial brain stimulation procedure on the patient, wherein a positioning of the transcranial brain stimulation procedure is determined at least in part on the one or more predicted locations of brain injury output by the machine-learned brain injury location model.

* * * * *